US012678091B2

(12) United States Patent
Lee

(10) Patent No.: US 12,678,091 B2
(45) Date of Patent: Jul. 14, 2026

(54) PERFUSION IMAGING-BASED NON-CONTACT AUTONOMIC NERVOUS SYSTEM RESPONSE MULTI-DIMENSIONAL BIO-SIGNAL MEASUREMENT SYSTEM AND METHOD

(71) Applicant: INDUSTRY ACADEMIC COOPERATION FOUNDATION KEIMYUNG UNIVERSITY, Daegu (KR)

(72) Inventor: Jong-Ha Lee, Daegu (KR)

(73) Assignee: INDUSTRY ACADEMIC COOPERATION FOUNDATION KEIMYUNG UNIVERSITY, Daegu (KR)

( * ) Notice: Subject to any disclaimer, the term of this patent is extended or adjusted under 35 U.S.C. 154(b) by 198 days.

(21) Appl. No.: 18/711,052

(22) PCT Filed: Nov. 15, 2022

(86) PCT No.: PCT/KR2022/018025
§ 371 (c)(1),
(2) Date: May 16, 2024

(87) PCT Pub. No.: WO2023/090828
PCT Pub. Date: May 25, 2023

(65) Prior Publication Data
US 2025/0000432 A1      Jan. 2, 2025

(30) Foreign Application Priority Data
Nov. 17, 2021    (KR) ........................ 10-2021-0158956

(51) Int. Cl.
*A61B 5/00* (2006.01)
*A61B 5/0205* (2006.01)
(Continued)

(52) U.S. Cl.
CPC .......... *A61B 5/4035* (2013.01); *A61B 5/0205* (2013.01); *A61B 5/0261* (2013.01);
(Continued)

(58) Field of Classification Search
CPC ....... A61B 5/00; A61B 5/0033; A61B 5/0075; A61B 5/0077; A61B 5/02; A61B 5/0205;
(Continued)

(56) References Cited

U.S. PATENT DOCUMENTS

2019/0000391 A1*   1/2019   De Haan .............. A61B 5/1102

FOREIGN PATENT DOCUMENTS

JP        2015527909 A      9/2015
JP        2019505263 A      2/2019
(Continued)

OTHER PUBLICATIONS

International search report of PCT/KR2022/018025, Mar. 2, 2023, English translation.

*Primary Examiner* — Michael T Rozanski
(74) *Attorney, Agent, or Firm* — STIP Law Group, LLC

(57) ABSTRACT

Proposed are a perfusion imaging-based non-contact autonomic nervous system response multi-dimensional bio-signal measurement system and method, the system including a light source, a multi-dimensional multi-spectral camera, and a measurement diagnosis part. The light source is configured to emit light outside a visible light region, for measuring a multi-dimensional bio-signal in a non-contact manner. The multi-dimensional multi-spectral camera is configured to photograph amplified reflected light reflected after emitted from the light source and generate an image sequence of the bio-signal accordingly. The measurement diagnosis part is configured to measure heart rate, oxygen saturation, blood flow per second, and blood pressure through image processing of the image sequence of the
(Continued)

bio-signal generated from photographing by the multi-dimensional multi-spectral camera.

14 Claims, 10 Drawing Sheets

(51) Int. Cl.
    *A61B 5/021*           (2006.01)
    *A61B 5/024*           (2006.01)
    *A61B 5/026*           (2006.01)
    *A61B 5/1455*         (2006.01)
(52) U.S. Cl.
    CPC .......... *A61B 5/14551* (2013.01); *A61B 5/021*
                 (2013.01); *A61B 5/02427* (2013.01)
(58) Field of Classification Search
    CPC ..... A61B 5/021; A61B 5/024; A61B 5/02416;
              A61B 5/02427; A61B 5/026; A61B
             5/0261; A61B 5/1455; A61B 5/14551;
                           A61B 5/4035
    See application file for complete search history.

(56)                    References Cited

FOREIGN PATENT DOCUMENTS

| | | | |
|----|----------------|----|---------|
| KR | 20070056925 | A | 6/2007 |
| KR | 101752560 | B1 | 6/2017 |
| KR | 20200001911 | A | 1/2020 |
| KR | 20200144893 | A | 12/2020 |
| KR | 20210085867 | A | 7/2021 |

\* cited by examiner

100

110

<u>130</u> measurement
diagnosis part

| image processor | ～131 |

| bio-signal measurement part | ～132 |

| diagnosis part | ～133 |

FIG. 15

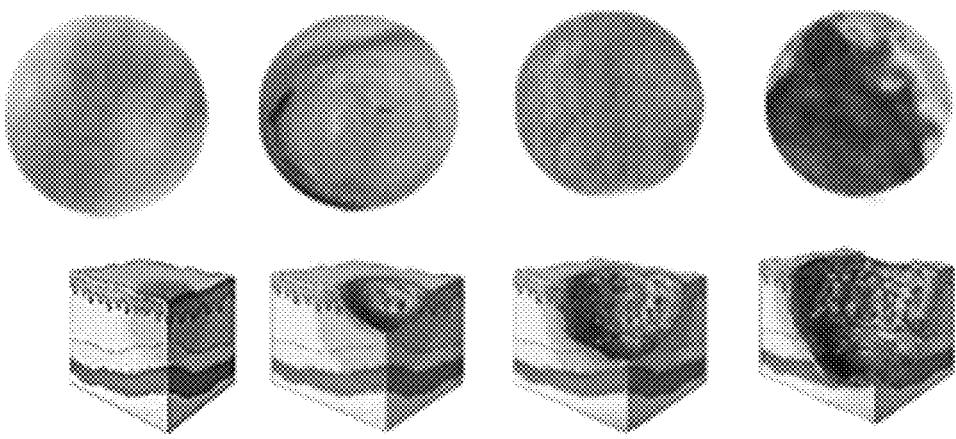

FIG. 16

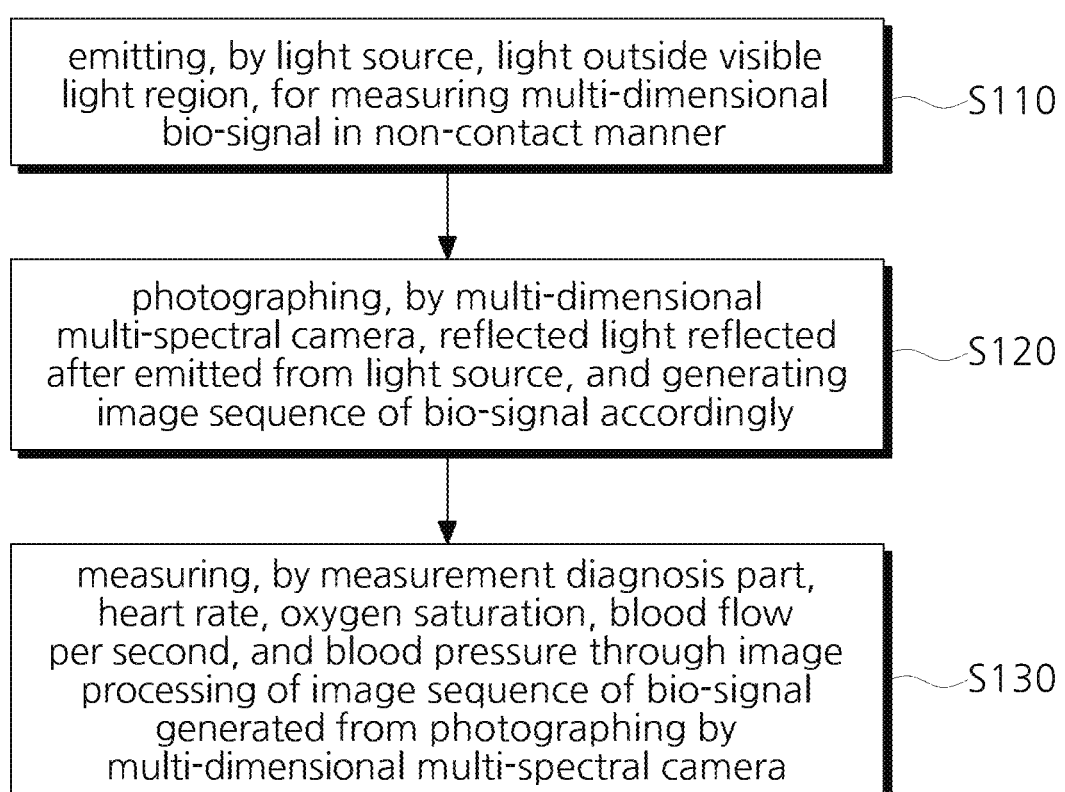

emitting, by light source, light outside visible light region, for measuring multi-dimensional bio-signal in non-contact manner — S110 photographing, by multi-dimensional multi-spectral camera, reflected light reflected after emitted from light source, and generating image sequence of bio-signal accordingly — S120 measuring, by measurement diagnosis part, heart rate, oxygen saturation, blood flow per second, and blood pressure through image processing of image sequence of bio-signal generated from photographing by multi-dimensional multi-spectral camera — S130

PERFUSION IMAGING-BASED NON-CONTACT AUTONOMIC NERVOUS SYSTEM RESPONSE MULTI-DIMENSIONAL BIO-SIGNAL MEASUREMENT SYSTEM AND METHOD

CROSS-REFERENCE TO RELATED APPLICATIONS

This application is the U.S. National Phase under 35 U.S.C. § 371 of International Application No. PCT/KR2022/018025, filed on Nov. 15, 2022, which in turn claims the benefit of Korean Application No. 10-2021-0158956, filed on Nov. 17, 2021, the disclosures of which are incorporated by reference into the present application.

TECHNICAL FIELD

The present disclosure relates to a multi-dimensional bio-signal measurement system and method. More particularly, the present disclosure relates to a perfusion imaging-based non-contact autonomic nervous system response multi-dimensional bio-signal measurement system and method.

BACKGROUND ART

Recently, new viral infections have emphasized the need for a non-face-to-face medical system that uses data-driven software to prevent, manage, and treat diseases, such as telemedicine and digital therapeutics. In response to this trend, research has been conducted on various methods to replace bio-signal measurement with traditional sensors. Systems developed to replace existing attachable sensors predict bio-signals on the basis of images in the visible light region.

However, these approaches suffer from various limitations. In order to maximize the effectiveness of the non-face-to-face medical system, it is necessary to accurately measure multiple bio-signals simultaneously in various environments, but most existing non-contact biometric systems can only measure a single bio-signal, such as heart rate, oxygen saturation, or blood pressure, and the accuracy of the systems is highly affected by external factors, such as external lighting. In addition, most blood pressure measurement methods calculate make calculation based on blood flow rate, which makes it difficult to realize a perfect non-contact system.

In this way, the existing non-contact biometric systems measure a single bio-signal individually, and most of the systems are designed to measure heart rate. In addition, multi-bio-signal measurement systems use a regular camera to perform measurement within the field of view, which is noise-sensitive, inaccurate, and prone to loss of feature points when bio-signals are measured. In particular, for oxygen saturation, existing systems use a channel separation method to measure oxygen saturation in the visible light region. This method uses the difference in light absorption wavelength between oxidized hemoglobin and hemoglobin. However, the difference in light absorption amount in the visible light region is small, so the calculation requires an amplification process, which involves many estimates and reduces accuracy.

In existing systems, bio-signal measurement is often impossible due to loss of feature points when a bio-signal measurement area is smaller than the full resolution. In addition, existing blood pressure measurement uses PTT, a method of estimating blood pressure from the time that it takes for the pulse to travel from the heart to the periphery. This requires measuring the pulse in two areas. To solve this problem, the existing systems are designed for partial contact. Korean Patent No. 10-1752560 and Korean Patent Application Publication No. 10-2007-0056925 are disclosed as documents in the related art.

DISCLOSURE

Technical Problem

The present disclosure has been made keeping in mind the above problems occurring in the previously proposed methods, and the present disclosure is directed to providing a perfusion imaging-based non-contact autonomic nervous system response multi-dimensional bio-signal measurement system and method, the system including: a light source configured to emit light outside a visible light region, for measuring a multi-dimensional bio-signal in a non-contact manner; a multi-dimensional multi-spectral camera configured to photograph amplified reflected light reflected after emitted from the light source, and generate an image sequence of the bio-signal accordingly; and a measurement diagnosis part configured to measure heart rate, oxygen saturation, blood flow per second, and blood pressure through image processing of the image sequence of the bio-signal generated from photographing by the multi-dimensional multi-spectral camera. Accordingly, the limitations of existing individual-bio-signal measurement systems are overcome, and the accuracy of bio-signal measurement and diagnosis can be increased through image processing excluding noise observed in the field of view, thereby further improving the efficiency and convenience of multi-dimensional bio-signal measurement.

In addition, the present disclosure is directed to providing a perfusion imaging-based non-contact autonomic nervous system response multi-dimensional bio-signal measurement system and method that are configured to measure a non-contact bio-signal using a multi-dimensional multi-spectral camera capable of reducing visible light noise, to measure heart rate, oxygen saturation, blood flow per second, and blood pressure in order, whereby a multi-dimensional complex bio-signal is used to enable that early diagnosis of lesions are difficult to measure quantitatively.

Technical Solution

In order to achieve the above objectives, according to an aspect of the present disclosure, there is provided a perfusion imaging-based non-contact autonomic nervous system response multi-dimensional bio-signal measurement system, the perfusion imaging-based non-contact autonomic nervous system response multi-dimensional bio-signal measurement system including:
  a light source configured to emit light outside a visible light region, for measuring a multi-dimensional bio-signal in a non-contact manner;
  a multi-dimensional multi-spectral camera configured to photograph amplified reflected light reflected after emitted from the light source, and generate an image sequence of the bio-signal accordingly; and
  a measurement diagnosis part configured to measure heart rate, oxygen saturation, blood flow per second, and blood pressure through image processing of the image sequence of the bio-signal generated from photographing by the multi-dimensional multi-spectral camera.

Preferably, the light source may be configured to emit the light outside the visible light region, for measuring the multi-dimensional bio-signal in a non-contact manner, and emit the light in two different wavelengths.

More preferably, the light source may include a red LED for emitting red light and an infrared LED for emitting infrared light, as the light in the two different wavelengths outside the visible light region, for measuring the multi-dimensional bio-signal in a non-contact manner.

Preferably, the multi-dimensional multi-spectral camera may be an infrared camera configured to photograph the amplified reflected light reflected after emitted from the light source 110 and generate the image sequence of the bio-signal.

Preferably, the measurement diagnosis part may be configured to measure the heart rate, the oxygen saturation, the blood flow per second, and the blood pressure through image processing of the image sequence of the bio-signal generated from photographing by the multi-dimensional multi-spectral camera, and may be configured to measure the heart rate by extracting valid pixels through clustering from the image sequence of the bio-signal generated from photographing by the multi-dimensional multi-spectral camera.

More preferably, the measurement diagnosis part may be configured to measure the oxygen saturation by receiving, from the multi-dimensional multi-spectral camera, the image sequence obtained by photographing the amplified reflected light obtained as the light is emitted alternately from the red LED and the infrared LED of the light source and is reflected.

Even more preferably, the measurement diagnosis part may be configured to measure the blood pressure without physical contact by using the measured heart rate and the measured oxygen saturation, and a change in the blood flow per second measured through a deep neural network based on a measured amount of reflected light.

Even more preferably, the measurement diagnosis part may include:

an image processor configured to perform signal processing on images of the image sequence of the bio-signal generated through photographing by the multi-dimensional multi-spectral camera;

a bio-signal measurement part configured to measure the heart rate, the oxygen saturation, and the blood pressure using the images subjected to signal processing by the image processor; and a diagnosis part configured to diagnose a lesion using the heart rate, the oxygen saturation, and the blood pressure measured by the bio-signal measurement part.

In order to achieve the above objectives, according to another aspect of the present disclosure, there is provided a perfusion imaging-based non-contact autonomic nervous system response multi-dimensional bio-signal measurement method, the perfusion imaging-based non-contact autonomic nervous system response multi-dimensional bio-signal measurement method including:

(1) emitting, by a light source, light outside a visible light region, for measuring a multi-dimensional bio-signal in a non-contact manner;

(2) photographing, by a multi-dimensional multi-spectral camera, reflected light reflected after emitted from the light source, and generating an image sequence of the bio-signal accordingly;

(3) measuring, by a measurement diagnosis part, heart rate, oxygen saturation, blood flow per second, and blood pressure through image processing of the image sequence of the bio-signal generated from photographing by the multi-dimensional multi-spectral camera.

Preferably, the light source may be configured to emit the light outside the visible light region, for measuring the multi-dimensional bio-signal in a non-contact manner, and emit the light in two different wavelengths.

More preferably, the light source may include a red LED for emitting red light and an infrared LED for emitting infrared light, as the light in the two different wavelengths outside the visible light region, for measuring the multi-dimensional bio-signal in a non-contact manner.

Preferably, the multi-dimensional multi-spectral camera may be an infrared camera configured to photograph amplified reflected light reflected after emitted from the light source 110 and generate the image sequence of the bio-signal.

Preferably, the measurement diagnosis part may be configured to measure the heart rate, the oxygen saturation, the blood flow per second, and the blood pressure through image processing of the image sequence of the bio-signal generated from photographing by the multi-dimensional multi-spectral camera, and may be configured to measure the heart rate by extracting valid pixels through clustering from the image sequence of the bio-signal generated from photographing by the multi-dimensional multi-spectral camera.

More preferably, the measurement diagnosis part may be configured to measure the oxygen saturation by receiving, from the multi-dimensional multi-spectral camera, the image sequence obtained by photographing the amplified reflected light obtained as the light is emitted alternately from the red LED and the infrared LED of the light source and is reflected.

Even more preferably, the measurement diagnosis part may be configured to measure the blood pressure without physical contact by using the measured heart rate and the measured oxygen saturation, and a change in the blood flow per second measured through a deep neural network based on a measured amount of reflected light.

Even more preferably, the measurement diagnosis part may include:

an image processor configured to perform signal processing on images of the image sequence of the bio-signal generated through photographing by the multi-dimensional multi-spectral camera;

a bio-signal measurement part configured to measure the heart rate, the oxygen saturation, and the blood pressure using the images subjected to signal processing by the image processor; and a diagnosis part configured to diagnose a lesion using the heart rate, the oxygen saturation, and the blood pressure measured by the bio-signal measurement part.

Advantageous Effects

According to the perfusion imaging-based non-contact measurement system and method proposed in the present disclosure, the system includes: a light source configured to emit light outside a visible light region, for measuring a multi-dimensional bio-signal in a non-contact manner; a multi-dimensional multi-spectral camera configured to photograph amplified reflected light reflected after emitted from the light source, and generate an image sequence of the bio-signal accordingly; and a measurement diagnosis part configured to measure heart rate, oxygen saturation, blood flow per second, and blood pressure through image processing of the image sequence of the bio-signal generated from photographing by the multi-dimensional multi-spectral camera. Accordingly, the limitations of existing individual-bio-signal measurement systems are overcome, and the accuracy of bio-signal measurement and diagnosis can be increased through image processing excluding noise observed in the field of view, thereby further improving the efficiency and convenience of multi-dimensional bio-signal measurement.

In addition, according to the perfusion imaging-based non-contact autonomic nervous system response multi-dimensional bio-signal measurement system and method of the present disclosure, a non-contact bio-signal is measured using the multi-dimensional multi-spectral camera capable of reducing visible light noise, and heart rate, oxygen saturation, blood flow per second, and blood pressure are measured in order, whereby a multi-dimensional complex bio-signal is used to enable early diagnosis of lesions that are difficult to measure quantitatively.

DESCRIPTION OF DRAWINGS

FIG. 15 is a diagram illustrating staged skin conditions of a bedsore in a perfusion imaging-based non-contact autonomic nervous system response multi-dimensional bio-signal measurement system according to an embodiment of the present disclosure.

FIG. 16 is a diagram illustrating the flow of a perfusion imaging-based non-contact autonomic nervous system response multi-dimensional bio-signal measurement method according to an embodiment of the present disclosure.

DESCRIPTION OF THE REFERENCE NUMERALS IN THE DRAWINGS

Figure 1:
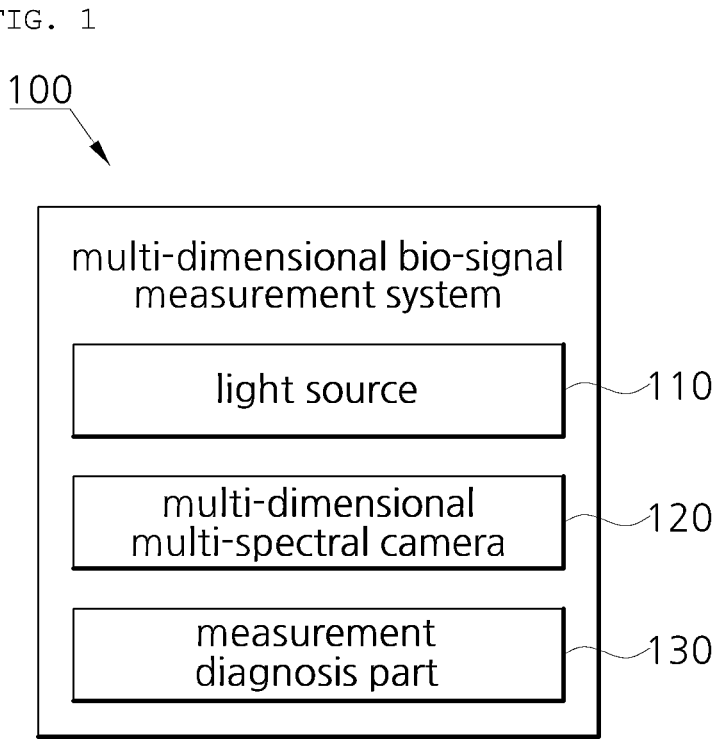
FIG. 1 is a functional block diagram illustrating the configuration of a perfusion imaging-based non-contact autonomic nervous system response multi-dimensional bio-signal measurement system according to an embodiment of the present disclosure.

100: multi-dimensional bio-signal measurement system of present disclosure
110: light source
111: red LED
112: infrared LED
120: multi-dimensional multi-spectral camera
130: measurement diagnosis part
131: image processor
132: bio-signal measurement part
133: diagnosis part
S110: emitting, by light source, light outside visible light region, for measuring multi-dimensional bio-signal in non-contact manner
S120: photographing, by multi-dimensional multi-spectral camera, reflected light reflected after emitted from light source, and generating image sequence of bio-signal accordingly
S130: measuring, by measurement diagnosis part, heart rate, oxygen saturation, blood flow per second, and blood pressure through image processing of image sequence of bio-signal generated from photographing by multi-dimensional multi-spectral camera

BEST MODE

Hereinafter, preferred embodiments of the present disclosure will be described in detail with reference to the accompanying drawings such that the present disclosure can be easily embodied by those skilled in the art to which the present disclosure belongs. However, in describing the preferred embodiments of the present disclosure in detail, if it is decided that a detailed description of the known function or configuration related to the present disclosure makes the subject matter of the present disclosure unclear, the detailed description will be omitted. In addition, throughout the drawings, the same reference numerals are used for parts having similar functions and operations.

Throughout the specification, when a part is referred to as being 'connected' to another part, it includes not only being 'directly connected', but also being 'indirectly connected' by interposing the other part therebetween. In addition, when a part 'includes' an element, this means that it further includes other elements, but does not exclude other elements, unless specifically stated otherwise.

Figure 2:
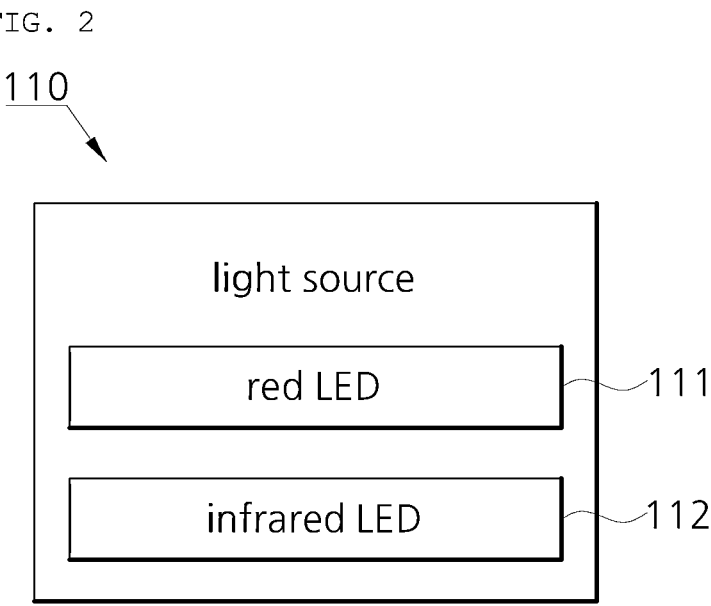
FIG. 2 is a functional block diagram illustrating the configuration of a light source of a perfusion imaging-based non-contact autonomic nervous system response multi-dimensional bio-signal measurement system according to an embodiment of the present disclosure.
Figures 3, 4:
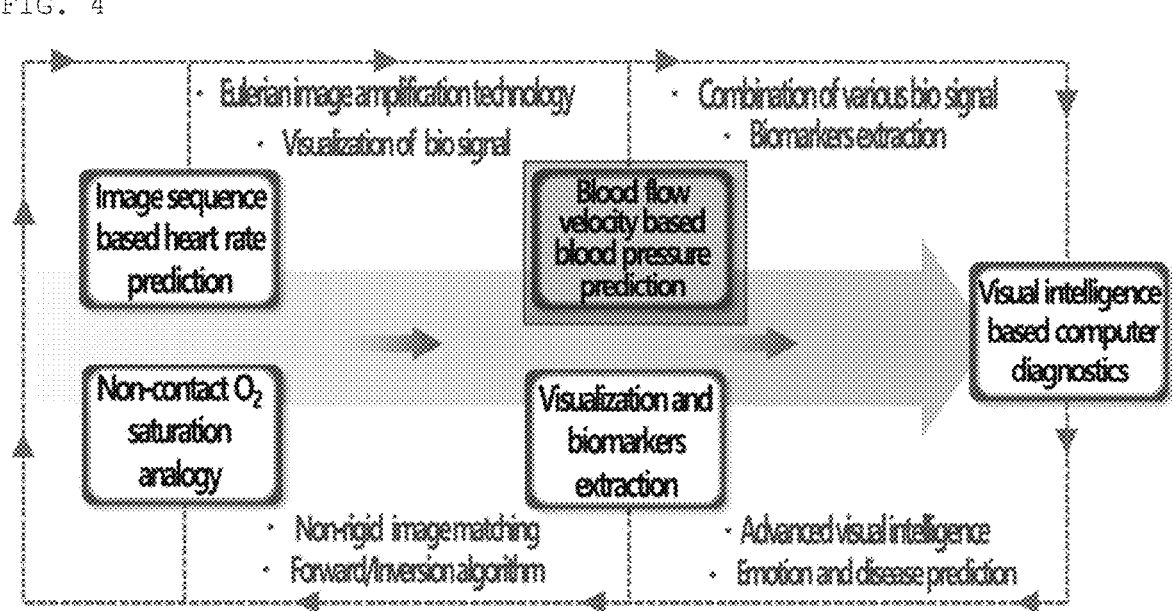
FIG. 3 is a functional block diagram illustrating the configuration of a measurement diagnosis part of a perfusion imaging-based non-contact autonomic nervous system response multi-dimensional bio-signal measurement system according to an embodiment of the present disclosure.
FIG. 4 is a diagram illustrating the concept of a perfusion imaging-based non-contact autonomic nervous system response multi-dimensional bio-signal measurement system according to an embodiment of the present disclosure.

FIG. 1 is a functional block diagram illustrating the configuration of a perfusion imaging-based non-contact autonomic nervous system response multi-dimensional bio-signal measurement system according to an embodiment of the present disclosure. FIG. 2 is a functional block diagram illustrating the configuration of a light source of a perfusion imaging-based non-contact autonomic nervous system response multi-dimensional bio-signal measurement system according to an embodiment of the present disclosure. FIG. 3 is a functional block diagram illustrating the configuration of a measurement diagnosis part of a perfusion imaging-based non-contact autonomic nervous system response multi-dimensional bio-signal 1 measurement system according to an embodiment of the present disclosure. FIG. 4 is a diagram illustrating the concept of a perfusion imaging-based non-contact autonomic nervous system response multi-dimensional bio-signal measurement system according to an embodiment of the present disclosure. As shown in FIGS. 1 to 4, a perfusion imaging-based non-contact autonomic nervous system response multi-dimensional bio-signal measurement system 100 according to an embodiment of the present disclosure includes a light source 110, a multi-dimensional multi-spectral camera 120, and a measurement diagnosis part 130. The light source 110 emits light outside a visible light region, for measuring a multi-dimensional bio-signal in a non-contact manner. The multi-dimensional multi-spectral camera 120 photographs amplified reflected light reflected after emitted from the light source 110, and generates an image sequence of the bio-signal accordingly. The measurement diagnosis part 130 measures heart rate, oxygen saturation, blood flow per second, and blood pressure through image processing of the image sequence of the bio-signal generated from photographing by the multi-dimensional multi-spectral camera 120. Hereinafter, a detailed configuration of a perfusion imaging-based non-contact autonomic nervous system response multi-dimensional bio-signal measurement system according to an embodiment of the present disclosure will be described with reference to the accompanying drawings.

Figure 5:
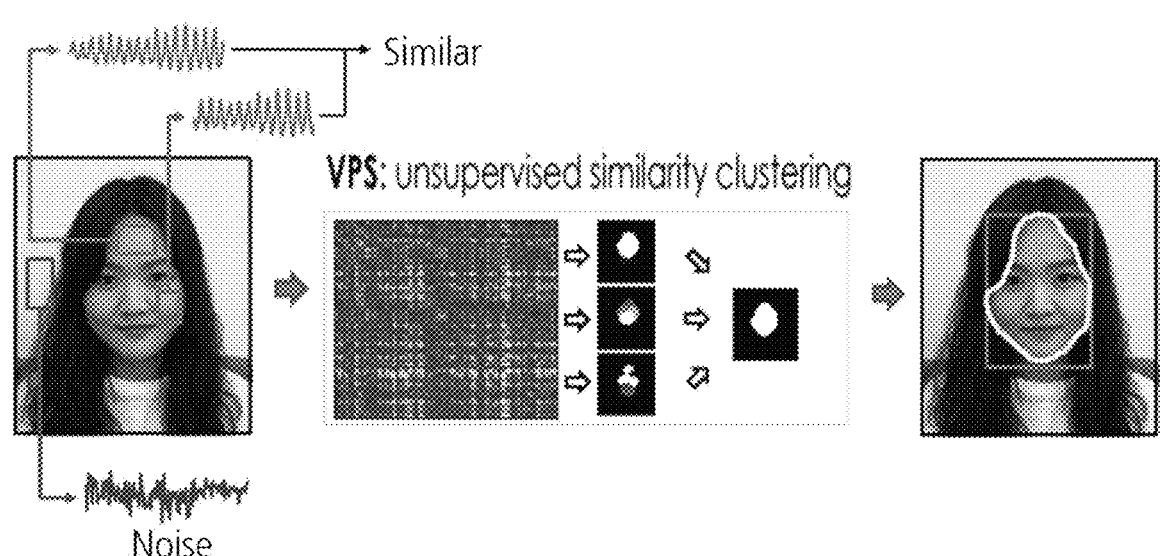
FIG. 5 is a diagram illustrating the form of extracting valid pixels through clustering, in image processing in a perfusion imaging-based non-contact autonomic nervous system response multi-dimensional bio-signal measurement system according to an embodiment of the present disclosure.
Figure 6:
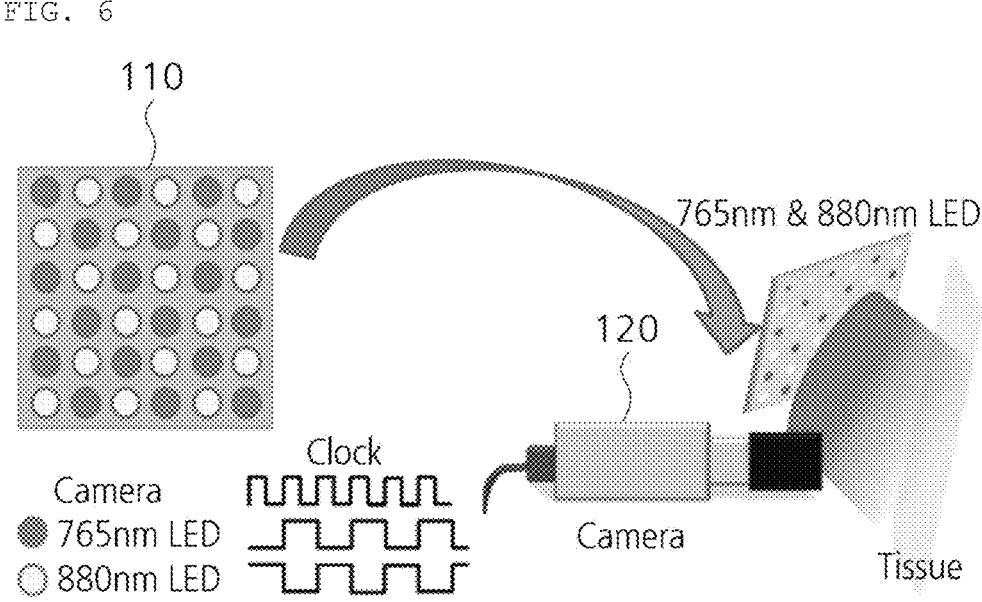
FIG. 6 is a diagram illustrating the form of oxygen saturation measurement in a perfusion imaging-based non-contact measurement system according to an embodiment of the present disclosure.
Figure 7:
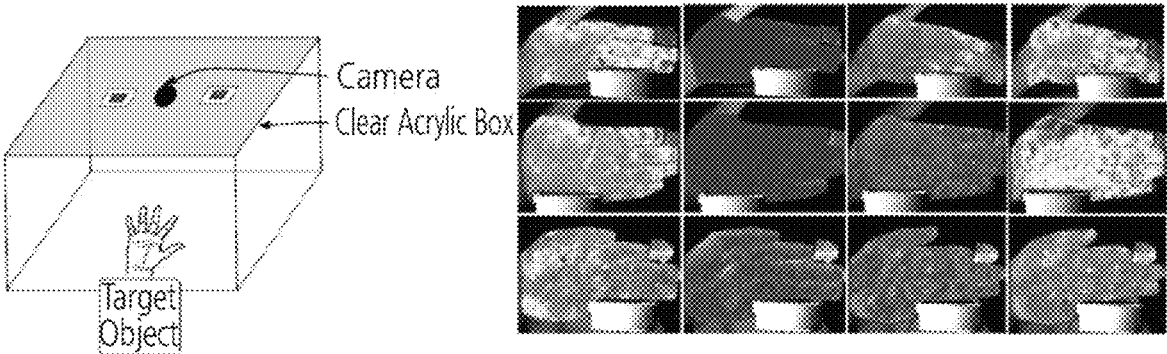
FIG. 7 is a diagram illustrating the form of perfusion measurement in a perfusion imaging-based non-contact autonomic nervous system response multi-dimensional bio-signal measurement system according to an embodiment of the present disclosure.
Figure 8:
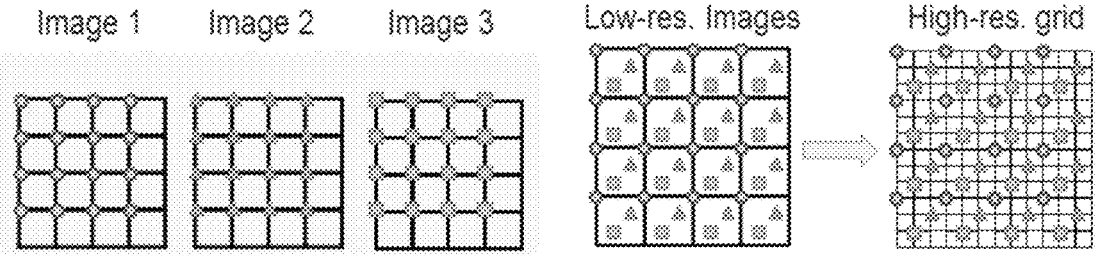
FIG. 8 is a diagram illustrating the form of multi-frame high-resolution image processing in a perfusion imaging-based non-contact autonomic nervous system response multi-dimensional bio-according to an embodiment of the signal measurement system present disclosure.

FIG. 5 is a diagram illustrating the form of extracting valid pixels through clustering, in image processing in a perfusion imaging-based non-contact autonomic nervous system response multi-dimensional bio-signal measurement system according to an embodiment of the present disclosure. FIG. 6 is a diagram illustrating the form of oxygen saturation measurement in a perfusion imaging-based non-contact autonomic nervous system response multi-dimensional bio-signal measurement system according to an embodiment of the present disclosure. FIG. 7 is a diagram illustrating the form of perfusion measurement in a perfusion imaging-based non-contact autonomic nervous system response multi-dimensional bio-signal measurement system according to an embodiment of the present disclosure. FIG. 8 is a diagram illustrating the form of multi-frame high-resolution image processing in a perfusion imaging-based non-contact autonomic nervous system response multi-dimensional bio-signal measurement system according to an embodiment of the present disclosure.

The light source 110 is an element for emitting light outside the visible light region, for measuring a multi-dimensional bio-signal in a non-contact manner. The light source 110 may emit light outside the visible light region, for measuring a multi-dimensional bio-signal in a non-contact manner, and may emit light in two different wavelengths.

In addition, the light source 110 may include a red LED 111 for emitting red light, and an infrared LED 112 for emitting infrared light which are light in the two different wavelengths outside the visible light region, for measuring a multi-dimensional bio-signal in a non-contact manner. The light source 110 may include LEDs of 765 nm and 880 nm. Herein, the light source 110 may have a structure in which the red LED 111 and the infrared LED 112 are arranged as shown in FIG. 6.

The multi-dimensional multi-spectral camera 120 is a camera for photographing amplified reflected light reflected after emitted from the light source 110, and generating an image sequence of a bio-signal accordingly. The multi-dimensional multi-spectral camera 120 may be an infrared camera for photographing amplified reflected light reflected after emitted from the light source 110 and generating an image sequence of a bio-signal. Herein, the image sequence of the bio-signal is perfusion images of a subject photographed through the multi-dimensional multi-spectral camera 120.

In addition, the multi-dimensional multi-spectral camera 120 is a camera for reducing visible light noise and measuring amplified reflected light obtained from light emitted from the light source 110. The multi-dimensional multi-spectral camera 120 may be physically separated from the measurement diagnosis part 130.

The measurement diagnosis part 130 is an element for measuring heart rate, oxygen saturation, blood flow per second, and blood pressure through image processing of the image sequence of the bio-signal generated from photographing by the multi-dimensional multi-spectral camera 120. The measurement diagnosis part 130 measures heart rate, oxygen saturation, blood flow per second, and blood pressure through image processing of the image sequence of the bio-signal generated from photographing by the multi-dimensional multi-spectral camera 120. As shown in FIG. 5, the measurement diagnosis part 130 may measure heart rate by extracting valid pixels through clustering from the image sequence of the bio-signal generated through photographing by the multi-dimensional multi-spectral camera 120.

In addition, as shown in FIG. 6, the measurement diagnosis part 130 may measure oxygen saturation by receiving, from the multi-dimensional multi-spectral camera 120, an image sequence obtained by photographing amplified reflected light obtained as light is emitted alternately from the red LED 111 and the infrared LED 112 of the light source 110 and is reflected.

In addition, the measurement diagnosis part 130 may measure blood pressure without physical contact by using the measured heart rate and oxygen saturation, and a change in blood flow per second measured through a deep neural network based on the measured amount of reflected light. Regarding such blood pressure measurement, as shown in FIG. 8 low-resolution images are superimposed to create a high-resolution image, and blood pressure is measured through diffusion of feature points in the high-resolution image. That is, regarding blood pressure measurement, blood pressure is calculated on the basis of blood flow rate and blood volume that affect blood pressure. Specifically, a regression model calculates blood pressure using the calculated diffusion vector mean, heart rate, oxygen saturation, and perfusion amplitude. The perfusion diffusion time may be measured by tracking contour feature points.

In addition, the measurement diagnosis part 130 may include an image processor 131, a bio-signal measurement part 132, and a diagnosis part 133. The image processor 131 performs signal processing on images of the image sequence of the bio-signal generated through photographing by the multi-dimensional multi-spectral camera 120. The bio-signal measurement part 132 measures heart rate, oxygen saturation, and blood pressure using the images subjected to signal processing by the image processor 131. The diagnosis part 133 diagnoses a lesion using the heart rate, the oxygen saturation, and the blood pressure measured by the bio-signal measurement part 132. Herein, the measurement diagnosis part 130 may function to enable early diagnosis of lesions that are difficult to measure quantitatively, by using a measured multi-dimensional complex bio-signal and a linkage technology that utilizes a statistical method, ensemble learning, and a deep learning technology based on the advancement of key element technologies of a bio-signal, image processing, and clinical information.

Figure 9:
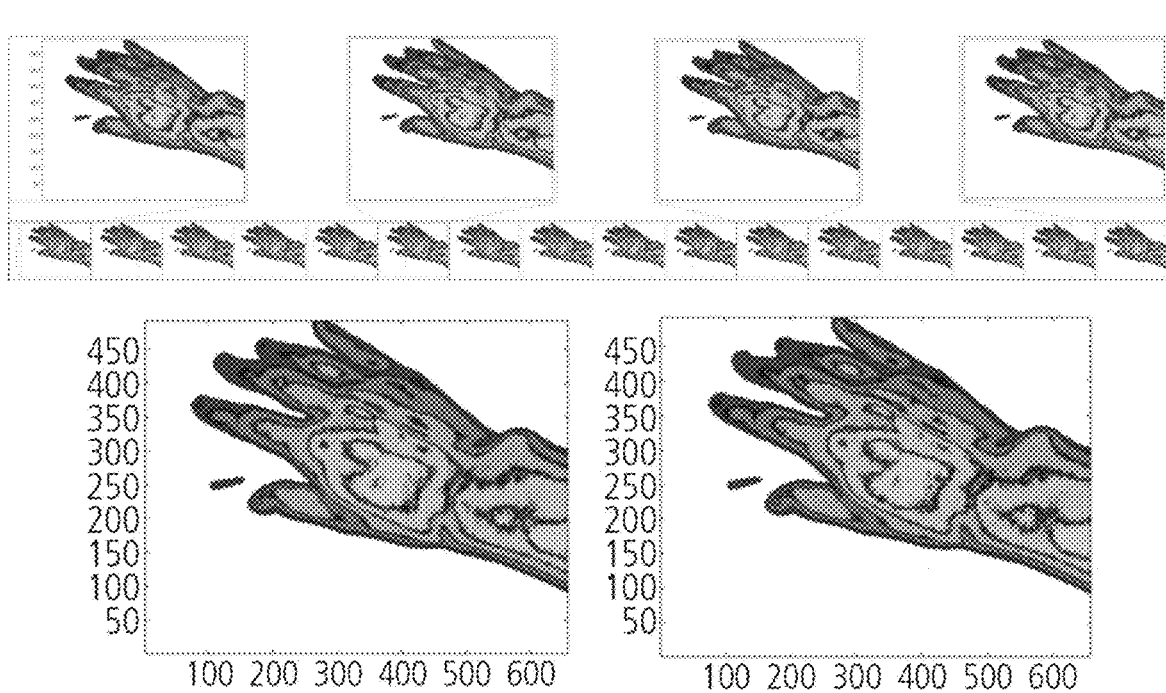
FIG. 9 is a diagram illustrating the form of measuring diffusion time by changing the location of a feature point in an image sequence in a perfusion imaging-based non-contact autonomic nervous system response multi-dimensional bio-signal measurement system according to an embodiment of the present disclosure.

FIG. 9 is a diagram illustrating the form of measuring diffusion time by changing the location of a feature point in an image sequence in a perfusion imaging-based non-contact autonomic nervous system response multi-dimensional bio-signal measurement system according to an embodiment of the present disclosure.

Figure 10:
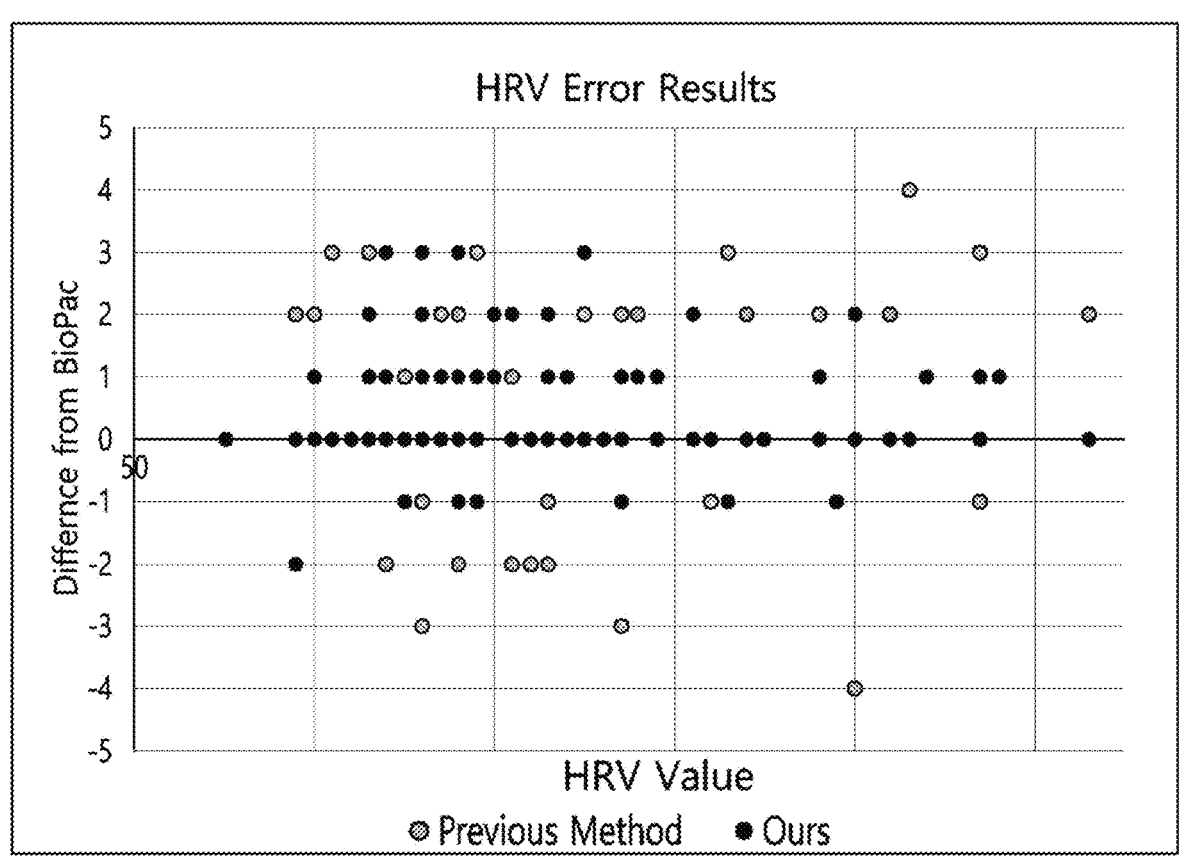
FIG. 10 is a diagram illustrating a heart rate measurement result of a perfusion imaging-based non-contact autonomic nervous system response multi-dimensional bio-signal measurement system according to an embodiment of the present disclosure.

FIG. 10 is a diagram illustrating a heart rate measurement result of a perfusion imaging-based non-contact autonomic nervous system response multi-dimensional bio-signal measurement system according to an embodiment of the present disclosure. As shown in FIG. 10, the difference between the actual heart rate and measured data values obtained by a camera was determined. The HRV values measured using an image sequence and the PPG pulse measured with Biopac MP150 were compared. As can see from the result, the mean accuracy error of the previous method was 0.96%, and that of the method according to the present disclosure was 0.63%.

Figure 11:
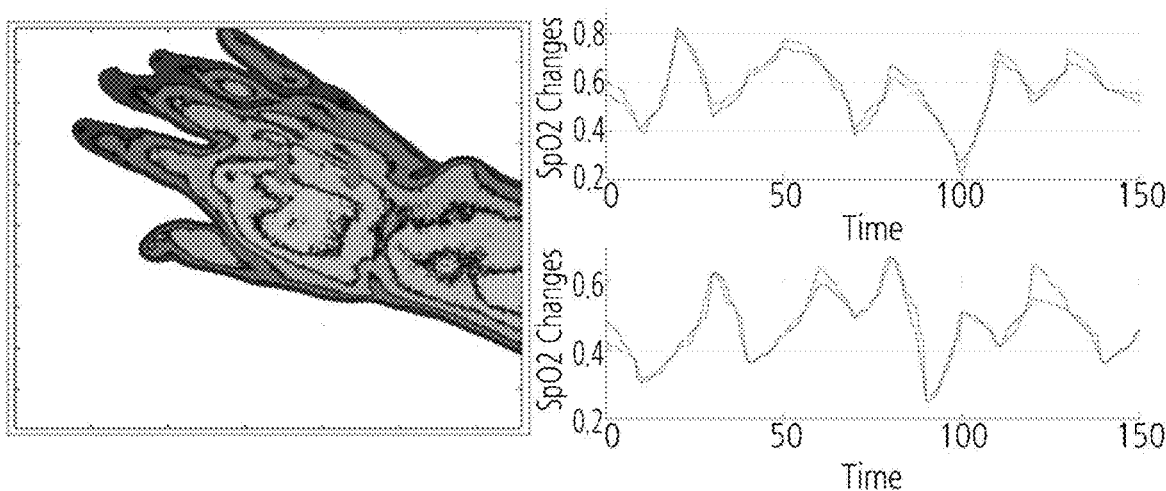
FIG. 11 is a diagram illustrating oxygen saturation measurement in a perfusion imaging-based non-contact autonomic nervous system response multi-dimensional bio-signal measurement system according to an embodiment of the present disclosure.

FIG. 11 is a diagram illustrating oxygen saturation measurement in a perfusion imaging-based non-contact autonomic nervous system response multi-dimensional bio-signal measurement system according to an embodiment of the present disclosure. As shown in FIG. 11, heart rate was calculated by changing an oxygen saturation contour (outline) value obtained using an IR camera. An image sequence was used to measure pulse oximetry with a non-contact method. A boundary region showing the range of variation in oxygen saturation was selected, and then change in pixel values was tracked, and the mean of the values was compared to BioPac and existing methods.

Figure 12:
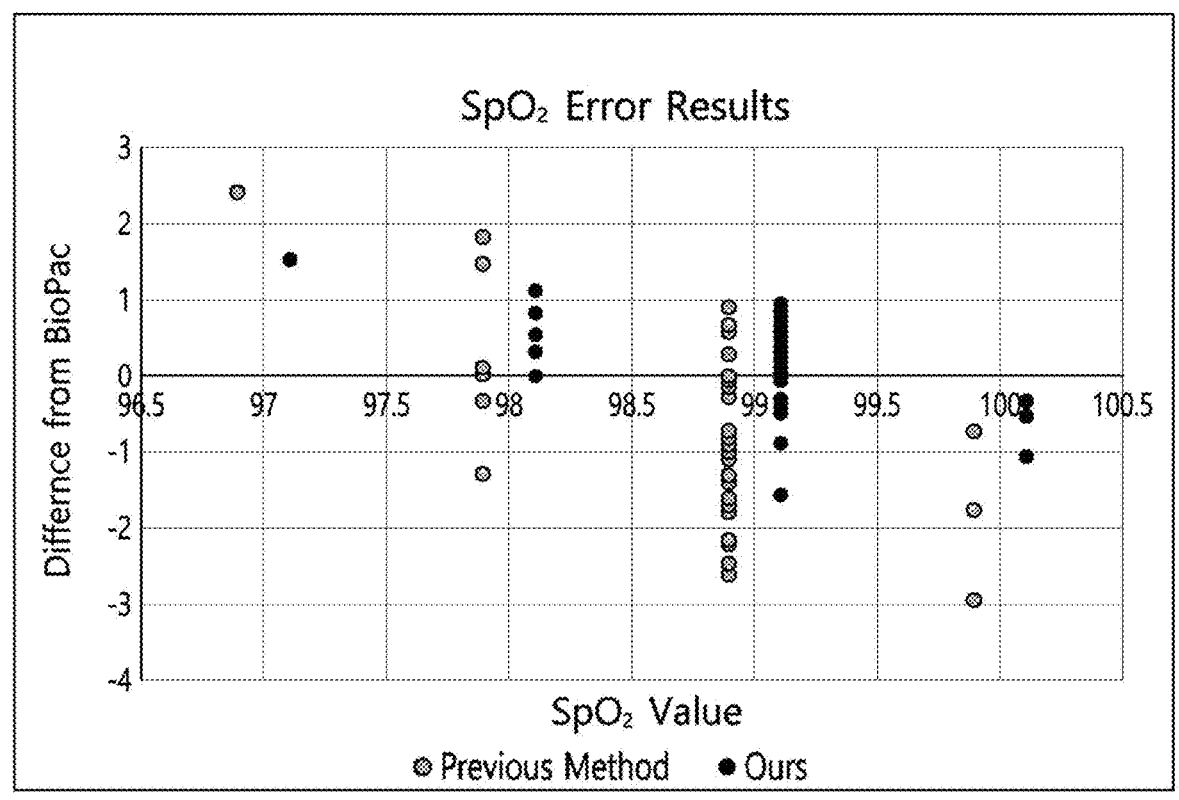
FIG. 12 is a diagram illustrating an oxygen saturation measurement result of a perfusion imaging-based non-contact measurement system according to an embodiment of the present disclosure.

FIG. 12 is a diagram illustrating an oxygen saturation measurement result of a perfusion imaging-based non-contact autonomic nervous system response multi-dimensional bio-signal measurement system according to an embodiment of the present disclosure. As shown in FIG. 12, the mean accuracy error of the existing method was 1.30%, and that of the method according to the present disclosure was 0.53%. In addition, the existing method showed a standard deviation value of 1.1 and the method according to the present disclosure showed a standard deviation value of 0.5.

Figure 13:
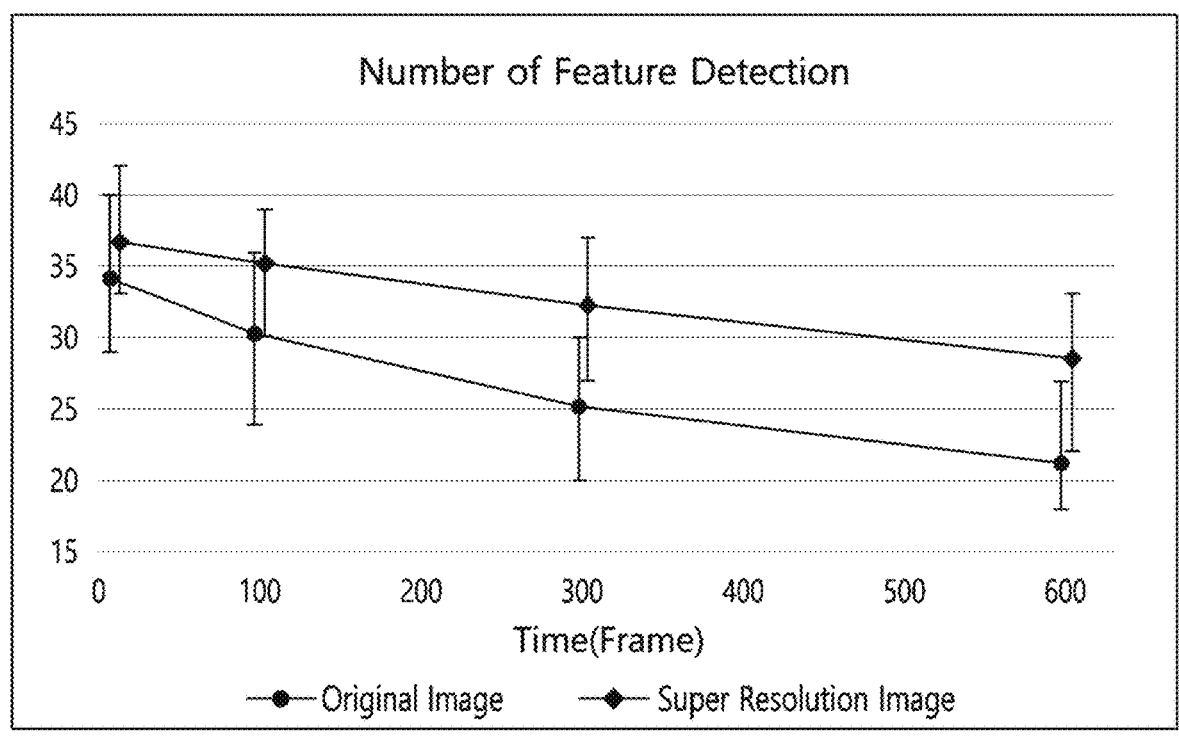
FIG. 13 is a diagram illustrating a feature point loss test result of a perfusion imaging-based non-contact autonomic nervous system response multi-dimensional bio-signal measurement system according to an embodiment of the present disclosure.

FIG. 13 is a diagram illustrating a feature point loss test result of a perfusion imaging-based non-contact autonomic nervous system response multi-dimensional bio-signal measurement system according to an embodiment of the present disclosure. As shown in FIG. 13, the number of feature points over time in the original image and that in the super resolution image were compared. The original image showed the feature point loss rate of 8.23% per 100 frames, and the super resolution image showed the loss rate of 4.04%.

Figure 14:
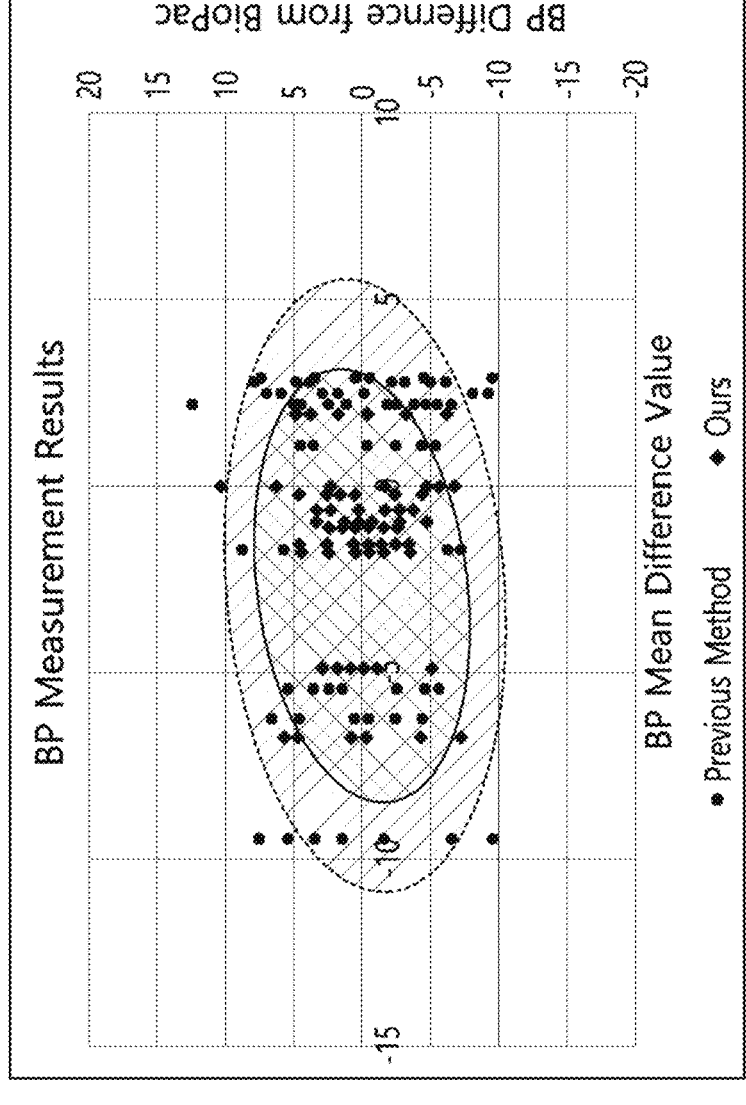
FIG. 14 is a diagram illustrating a blood pressure measurement test result of a perfusion imaging-based non-contact autonomic nervous system response multi-dimensional bio-signal system according to an embodiment of the present measurement disclosure.
Figure 14:
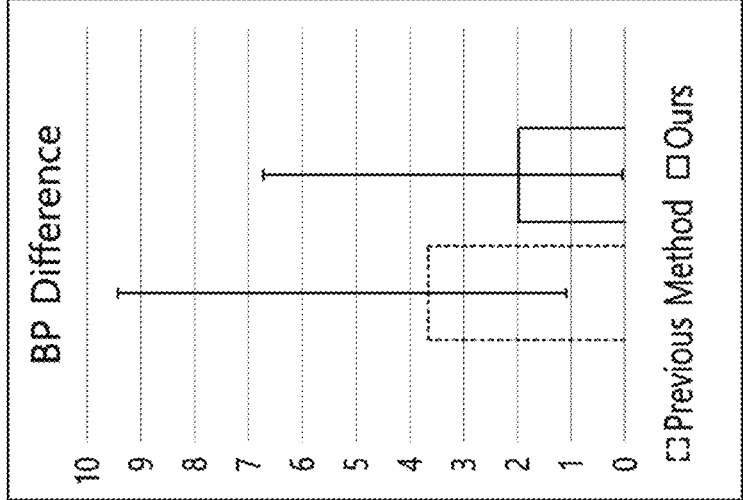

FIG. 14 is a diagram illustrating a blood pressure measurement test result of a perfusion imaging-based non-contact autonomic nervous system response multi-dimensional bio-signal measurement system according to an embodiment of the present disclosure. As shown in FIG. 14, a comparison to a cuff-based method, which is the standard method in the medical field, and a visible camera-based method showed that the mean error of blood pressure was 2.07%, representing a 3.86% improvement over the existing method.

FIG. 15 is a diagram illustrating staged skin conditions of a bedsore in a perfusion imaging-based non-contact autonomic nervous system response multi-dimensional bio-signal measurement system according to an embodiment of the present disclosure. As shown in FIG. 15, when an injury occurs, changes in skin density or blood volume cause changes in blood perfusion, and resulting injuries and bedsores may be detected.

In this way, in FIG. 16, to overcome the limitations of existing non-contact systems, a perfusion imaging-based non-contact autonomic nervous system response multi-dimensional bio-signal measurement system according to an embodiment of the present disclosure uses a multi-spectral camera to exclude noise observed in the field of view and measure blood perfusion to improve the accuracy of bio-signal measurement. In addition, to overcome the limitations of measurement regions, clustering and super resolution techniques were used. As a result, the heart rate measurement error rate was 0.63% and the oxygen saturation measurement error rate was 0.53%, which is an improvement over the existing method. Blood pressure measurement showed the mean error value of 0.207% and bio-signal measurement was improved by 50~60% over the existing method.

FIG. 16 is a diagram illustrating the flow of a perfusion imaging-based non-contact autonomic nervous system response multi-dimensional bio-signal method measurement according to an embodiment of the present disclosure. As shown in FIG. 16, a perfusion imaging-based non-contact autonomic nervous system response multi-dimensional bio-signal measurement method according to an embodiment of the present disclosure includes: emitting, by a light source, light outside a visible light region, for measuring a multi-dimensional bio-signal in a non-contact manner in step S110; photographing, by a multi-dimensional multi-spectral camera, reflected light reflected after emitted from the light source, and generating an image sequence of the bio-signal accordingly in step S120; and measuring, by a measurement diagnosis part, heart rate, oxygen saturation, blood flow per second, and blood pressure through image processing of the image sequence of the bio-signal generated from photographing by the multi-dimensional multi-spectral camera in step S130.

In step S110, the light source 110 emits light outside the visible light region, for measuring a multi-dimensional bio-signal in a non-contact manner. The light source 110 in step S110 may emit light outside the visible light region, for measuring a multi-dimensional bio-signal in a non-contact manner, and may emit light in two different wavelengths.

In addition, the light source 110 may include a red LED 111 for emitting red light, and an infrared LED 112 for emitting infrared light which are light in the two different wavelengths outside the visible light region, for measuring a multi-dimensional bio-signal in a non-contact manner. The light source 110 may include LEDs of 765 nm and 880 nm. Herein, the light source 110 may have a structure in which the red LED 111 and the infrared LED 112 are arranged as shown in FIG. 6.

In step S120, the multi-dimensional multi-spectral camera 120 photographs reflected light reflected after emitted from the light source 110, and generates an image sequence of a bio-signal accordingly. The multi-dimensional multi-spectral camera 120 in step S120 may be an infrared camera for photographing amplified reflected light reflected after emitted from the light source 110 and generating an image sequence of a bio-signal. Herein, the image sequence of a bio-signal is perfusion images of a subject photographed through the multi-dimensional multi-spectral camera 120.

In addition, the multi-dimensional multi-spectral camera 120 is a camera for reducing visible light noise and measuring amplified reflected light obtained from light emitted from the light source 110. The multi-dimensional multi-spectral camera 120 may be physically separated from the measurement diagnosis part 130.

In step S130, the measurement diagnosis part 130 measures heart rate, oxygen saturation, blood flow per second, and blood pressure through image processing of the image sequence of the bio-signal generated from photographing by the multi-dimensional multi-spectral camera 120. The measurement diagnosis part 130 in step S130 measures heart rate, oxygen saturation, blood flow per second, and blood pressure through image processing of the image sequence of the bio-signal generated from photographing by the multi-dimensional multi-spectral camera 120. As shown in FIG. 5, the measurement diagnosis part 130 may measure heart rate by extracting valid pixels through clustering from the image sequence of the bio-signal generated through photographing by the multi-dimensional multi-spectral camera 120.

In addition, as shown in FIG. 6, the measurement diagnosis part 130 may measure oxygen saturation by receiving, from the multi-dimensional multi-spectral camera 120, an image sequence obtained by photographing amplified reflected light obtained as light is emitted alternately from the red LED 111 and the infrared LED 112 of the light source 110 and is reflected.

In addition, the measurement diagnosis part 130 may measure blood pressure without physical contact by using the measured heart rate and oxygen saturation, and a change in blood flow per second measured through a deep neural network based on the measured amount of reflected light. Regarding such blood pressure measurement, as shown in FIG. 8, low-resolution images are superimposed to create a high-resolution image, and blood pressure is measured through diffusion of feature points in the high-resolution image. That is, regarding blood pressure measurement, blood pressure is calculated on the basis of blood flow rate and blood volume that affect blood pressure. Specifically, a regression model calculates blood pressure using the calculated diffusion vector mean, heart rate, oxygen saturation, and perfusion amplitude.

In addition, the measurement diagnosis part 130 may include an image processor 131, a bio-signal measurement part 132, and a diagnosis part 133. The image processor 131 performs signal processing on images of the image sequence of the bio-signal generated through photographing by the multi-dimensional multi-spectral camera 120. The bio-signal measurement part 132 measures heart rate, oxygen saturation, and blood pressure using the images subjected to signal processing by the image processor 131. The diagnosis part 133 diagnoses a lesion using the heart rate, the oxygen saturation, and the blood pressure measured by the bio-signal measurement part 132. That is, the measurement diagnosis part 130 may function to enable early diagnosis of lesions that are difficult to measure quantitatively, by using a measured multi-dimensional complex bio-signal and a linkage technology that utilizes a statistical method, ensemble learning, and a deep learning technology based on the advancement of key element technologies of a bio-signal, image processing, and clinical information.

As described above, a perfusion imaging-based non-contact autonomic nervous system response multi-dimensional bio-signal measurement system and method according to an embodiment of the present disclosure are configured to include: a light source configured to emit light outside a visible light region, for measuring a multi-dimensional bio-signal in a non-contact manner; a multi-dimensional multi-spectral camera configured to photograph amplified reflected light reflected after emitted from the light source, and generate an image sequence of the bio-signal accordingly; and a measurement diagnosis part configured to measure heart rate, oxygen saturation, blood flow per second, and blood pressure through image processing of the image sequence of the bio-signal generated from photographing by the multi-dimensional multi-spectral camera. Accordingly, the limitations of existing individual-bio-signal measurement systems are overcome, and the accuracy of bio-signal measurement and diagnosis can be increased through image processing excluding noise observed in the field of view, thereby further improving the efficiency and convenience of multi-dimensional bio-signal measurement. In particular, a non-contact bio-signal is measured using the multi-dimensional multi-spectral camera capable of reducing visible light noise, and heart rate, oxygen saturation, blood flow per second, and blood pressure are measured in order, whereby a multi-dimensional complex bio-signal is used to enable early diagnosis of lesions that are difficult to measure quantitatively.

Various modifications or applications of the above-described present disclosure may be made by those skilled in the art to which the present disclosure belongs, and the scope of the technical idea according to the present disclosure should be defined by the following claims.

The invention claimed is:

1. A perfusion imaging-based non-contact autonomic nervous system response multi-dimensional bio-signal measurement system, comprising:

a light source configured to emit in at least two different wavelengths, for measuring a multi-dimensional bio-signal in a non-contact manner;

a multi-dimensional multi-spectral camera configured to photograph amplified reflected light reflected after emission from the light source, and generate an image sequence of the bio-signal; and a processor configured to receive the image sequence from the multi-dimensional multi-spectral camera and to: measure heart rate, oxygen saturation, blood flow per second, and blood pressure through image processing of the image sequence; generate a high-resolution image by superimposing low-resolution images included in the image sequence; track contour feature points in the high-resolution image to determine perfusion diffusion time; and calculate the blood pressure using diffusion vector mean, the heart rate, the oxygen saturation, and perfusion amplitude.

2. The perfusion imaging-based non-contact autonomic nervous system response multi-dimensional bio-signal measurement system of claim 1, wherein the light source is configured to emit the light at about 765 nm and about 880 nm.

3. The perfusion imaging-based non-contact autonomic nervous system response multi-dimensional bio-signal measurement system of claim 2, wherein the light source comprises a first LED configured to emit red light and a second LED configured to emit infrared light.

4. The perfusion imaging-based non-contact autonomic nervous system response multi-dimensional bio-signal measurement system of claim 1, wherein the multi-dimensional multi-spectral camera is an infrared camera.

5. The perfusion imaging-based non-contact autonomic nervous system response multi-dimensional bio-signal measurement system of claim 1, wherein the processor is configured to measure the heart rate by extracting valid pixels through clustering from the image sequence.

6. The perfusion imaging-based non-contact autonomic nervous system response multi-dimensional bio-signal measurement system of claim 5, wherein the processor is configured to measure the oxygen saturation by using the image sequence obtained as the light is emitted alternately from the first LED and the second LED and is reflected.

7. The perfusion imaging-based non-contact autonomic nervous system response multi-dimensional bio-signal measurement system of claim 6, wherein the processor is configured to measure the blood pressure without physical contact by using the measured heart rate, the measured oxygen saturation, and a change in the blood flow per second measured through a deep neural network based on a measured amount of reflected light.

8. A perfusion imaging-based non-contact autonomic nervous system response multi-dimensional bio-signal measurement method, comprising:

emitting, by a light source, light in at least two different wavelengths for measuring a multi-dimensional bio-signal in a non-contact manner;

photographing, by a multi-dimensional multi-spectral camera, amplified reflected light reflected after emission from the light source, and generating an image sequence of the bio-signal; and processing, by a processor, the image sequence to:

measure heart rate, oxygen saturation, blood flow per second, and blood pressure through image processing of the image sequence; generate a high-resolution image by superimposing low-resolution images included in the image sequence;

track contour feature points in the high-resolution image to determine perfusion diffusion time; and calculate the blood pressure using a diffusion vector mean, the heart rate, the oxygen saturation, and perfusion amplitude.

9. The perfusion imaging-based non-contact autonomic nervous system response multi-dimensional bio-signal measurement method of claim 8, wherein the light is emitted at about 765 nm and about 880 nm.

10. The perfusion imaging-based non-contact autonomic nervous system response multi-dimensional bio-signal measurement method of claim 9, wherein the light source comprises a first LED configured to emit red light and a second LED configured to emit infrared light.

11. The perfusion imaging-based non-contact autonomic nervous system response multi-dimensional bio-signal measurement method of claim 8, wherein the multi-dimensional multi-spectral camera is an infrared camera.

12. The perfusion imaging-based non-contact autonomic nervous system response multi-dimensional bio-signal measurement method of claim 8, wherein the heart rate is measured by extracting valid pixels through clustering from the image sequence.

13. The perfusion imaging-based non-contact autonomic nervous system response multi-dimensional bio-signal measurement method of claim 12, wherein the oxygen saturation is measured by using the image sequence obtained as the light is emitted alternately from the first LED and the second LED and is reflected.

14. The perfusion imaging-based non-contact autonomic nervous system response multi-dimensional bio-signal measurement method of claim 13, wherein the blood pressure is measured without physical contact by using the measured heart rate, the measured oxygen saturation, and a change in the blood flow per second measured through a deep neural network based on a measured amount of reflected light.

\* \* \* \* \*